(12) United States Patent
Lee et al.

(10) Patent No.: US 12,343,553 B2
(45) Date of Patent: Jul. 1, 2025

(54) ELECTRONIC DEVICE AND OPERATION METHOD THEREOF FOR INCREASING TREATMENT EFFECT ON TARGET AREA

(71) Applicant: InnoLux Corporation, Miao-Li County (TW)

(72) Inventors: Chun-Kai Lee, Miao-Li County (TW); Cheng-Hsu Chou, Miao-Li County (TW); Fang-Iy Wu, Miao-Li County (TW)

(73) Assignee: INNOLUX CORPORATION, Miao-Li County (TW)

( * ) Notice: Subject to any disclaimer, the term of this patent is extended or adjusted under 35 U.S.C. 154(b) by 461 days.

(21) Appl. No.: 17/693,647

(22) Filed: Mar. 14, 2022

(65) Prior Publication Data

US 2022/0339461 A1     Oct. 27, 2022

Related U.S. Application Data

(60) Provisional application No. 63/177,990, filed on Apr. 22, 2021.

(30) Foreign Application Priority Data

Dec. 7, 2021    (CN) .......................... 202111483686.0

(51) Int. Cl.
*A61N 5/06*    (2006.01)
(52) U.S. Cl.
CPC ........ *A61N 5/06* (2013.01); *A61N 2005/0626* (2013.01); *A61N 2005/065* (2013.01); *A61N 2005/0652* (2013.01)
(58) Field of Classification Search
None
See application file for complete search history.

(56) References Cited

U.S. PATENT DOCUMENTS

| 5,944,748 | A  | * | 8/1999  | Mager ................. A61N 5/0601 606/9 |
| 2007/0239143 | A1 |   | 10/2007 | Altshuler et al. |
| 2010/0100160 | A1 | * | 4/2010  | Edman .................... A61B 5/444 607/88 |
| 2015/0190651 | A1 | * | 7/2015  | Jayavanth ............ A61N 5/0621 607/90 |
| 2016/0346564 | A1 | * | 12/2016 | Burgmann ............. H05B 47/10 |
| 2020/0360547 | A1 | * | 11/2020 | Smith ....................... A61L 2/24 |

FOREIGN PATENT DOCUMENTS

| CN | 102348425 A |   | 2/2012 |
| CN | 103654728 A |   | 3/2014 |
| CN | 105852806 A |   | 8/2016 |
| CN | 112274785 A | * | 1/2021 |

OTHER PUBLICATIONS

Chinese language office action dated Jan. 9, 2023, issued in application No. TW 111111249.

* cited by examiner

*Primary Examiner* — Michael W Kahelin
*Assistant Examiner* — Luke M Stanley
(74) *Attorney, Agent, or Firm* — McClure, Qualey & Rodack, LLP

(57) ABSTRACT

An electronic device includes a plurality of treatment components. The treatment components include a first treatment component and a second treatment component, wherein the first treatment component and the second treatment component are independently controlled. Therefore, the convenience of use may be increased, or the treatment effect on the target area may be increased.

17 Claims, 7 Drawing Sheets

ELECTRONIC DEVICE AND OPERATION METHOD THEREOF FOR INCREASING TREATMENT EFFECT ON TARGET AREA

CROSS REFERENCE TO RELATED APPLICATIONS

This application claims priority of U.S. Provisional Application No. 63/177,990, filed Apr. 22, 2021, and China Patent Application No. 202111483686.0, filed on Dec. 7, 2021, the entirety of which is incorporated by reference herein.

BACKGROUND OF THE DISCLOSURE

Field of the Disclosure

The disclosure relates to an electronic device, and in particular, to an electronic device and an operation method thereof.

Description of the Related Art

Light-emitting components of conventional phototherapy devices may generate light and deliver that light to an affected part of the user's body to provide treatment. However, a phototherapy device provides light of a fixed strength to the affected part of the user's body, and the strength of the light from the light-emitting components may not be adjusted according to the state of the affected body part, thereby decreasing the convenience of use and the effectiveness of the treatment. Therefore, a new design for a circuit structure is needed to improve the problem described above.

BRIEF SUMMARY OF THE DISCLOSURE

An embodiment of the disclosure provides an electronic device, which includes a plurality of treatment components. The treatment components include a first treatment component and a second treatment component, wherein the first treatment component and the second treatment component are independently controlled.

An embodiment of the disclosure provides an operation method of an electronic device, which includes the following steps. A substrate is provided. A plurality of treatment components is provided on the substrate, wherein treatment components includes a first treatment component and a second treatment component, and the first treatment component and the second treatment component provide signals with different parameters at the same time.

BRIEF DESCRIPTION OF THE DRAWINGS

The disclosure can be fully understood by reading the subsequent detailed description and examples with references made to the accompanying drawings, wherein.

DETAILED DESCRIPTION OF THE DISCLOSURE

Figure 1:
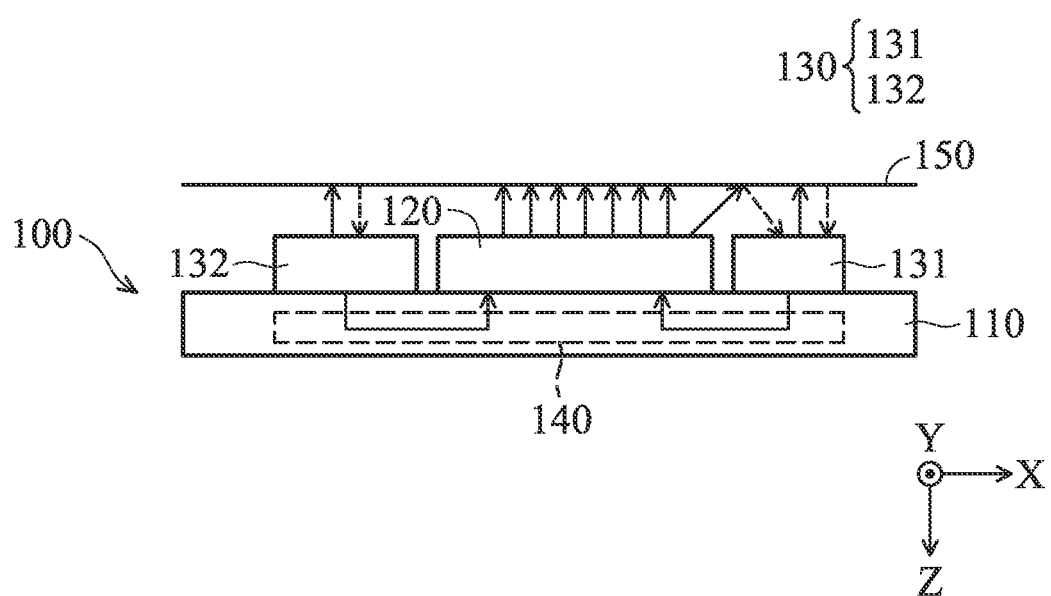
FIG. 1 is a schematic view of a part of an electronic device according to an embodiment of the disclosure.

In order to make objects, features and advantages of the disclosure more obvious and easily understood, the embodiments are described below, and the detailed description is made in conjunction with the drawings. In order to help the reader to understand the drawings, the multiple drawings in the disclosure may merely depict a part of the entire device, and the specific components in the drawing are not drawn to scale.

The specification of the disclosure provides various embodiments to illustrate the technical features of the various embodiments of the disclosure. The configuration, quantity, and size of each component in the embodiments are for illustrative purposes only, and are not intended to limit the disclosure. In addition, if the reference number of a component in the embodiments and the drawings appears repeatedly, it is for the purpose of simplifying the description, and does not mean to imply a relationship between different embodiments.

Furthermore, use of ordinal terms such as "first", "second", etc., in the specification and the claims to describe a claim element does not by itself connote and represent the claim element having any previous ordinal term, and does not represent the order of one claim element over another or the order of the manufacturing method, either. The ordinal terms are used merely as labels to distinguish one claim element having a certain name from another element having the same name.

In the disclosure, the technical features of the various embodiments may be replaced or combined with each other to complete other embodiments without being mutually exclusive.

In some embodiments of the disclosure, unless specifically defined, the term "coupled" may include any direct and indirect means of electrical connection.

In the text, the terms "substantially" or "approximately" usually means within 20%, or within 10%, or within 5%, or within 3%, or within 2%, or within 1%, or within 0.5% of a given value or range. The quantity given here is an approximate quantity. That is, without the specific description of "substantially" or "approximately", the meaning of "substantially" or "approximately" may still be implied.

The "including" mentioned in the entire specification and claims is an open term, so it should be interpreted as "including or comprising but not limited to".

Furthermore, "connected or "coupled" herein includes any direct and indirect connection means. Therefore, an element or layer is referred to as being "connected to" or "coupled to" another element or layer, the element or layer can be directly on, connected or coupled to another element or layer or intervening elements or layers may be present. When an element is referred to as being "directly connected to" or "directly coupled to" another element or layer, there are no intervening elements or layers present. If the text describes that a first device on a circuit is coupled to a second device, it indicates that the first device may be directly electrically connected to the second device. When the first device is directly electrically connected to the second device, the first device and the second device are only connected through conductive lines or passive elements (such as resistors, capacitors, etc.), and no other electronic elements are connected between the first device and the second device.

In an embodiment, the electronic device may include a display device, a backlight device, an antenna device, a sensing device, a splicing device or a therapeutic diagnosis device, but the disclosure is not limited thereto. The electronic device may be a bendable or flexible electronic device. The display device may be a non-self-luminous type display device or a self-luminous type display device. The antenna device may be a liquid-crystal type antenna device or a non-liquid-crystal type antenna device, and the sensing device may be a sensing device that senses capacitance, light, heat or ultrasound, but the disclosure is not limited thereto. The electronic component may include a passive component and an active component, such as a capacitor, a resistor, an inductor, a diode, a transistor, etc. The diode may include a light-emitting diode or a photodiode. The light-emitting diode may include, for example, an organic light-emitting diode (OLED), a mini LED, a micro LED or a quantum dot LED, but the disclosure is not limited thereto. The splicing device may be, for example, a display splicing device or an antenna splicing device, but the disclosure is not limited thereto. It should be noted that the electronic device may be any arrangement and combination of the above devices, but the disclosure is not limited thereto. Hereinafter, the display device will be used as an electronic device or a splicing device to illustrate to the content of the disclosure, but the disclosure is not limited thereto.

Figure 2:
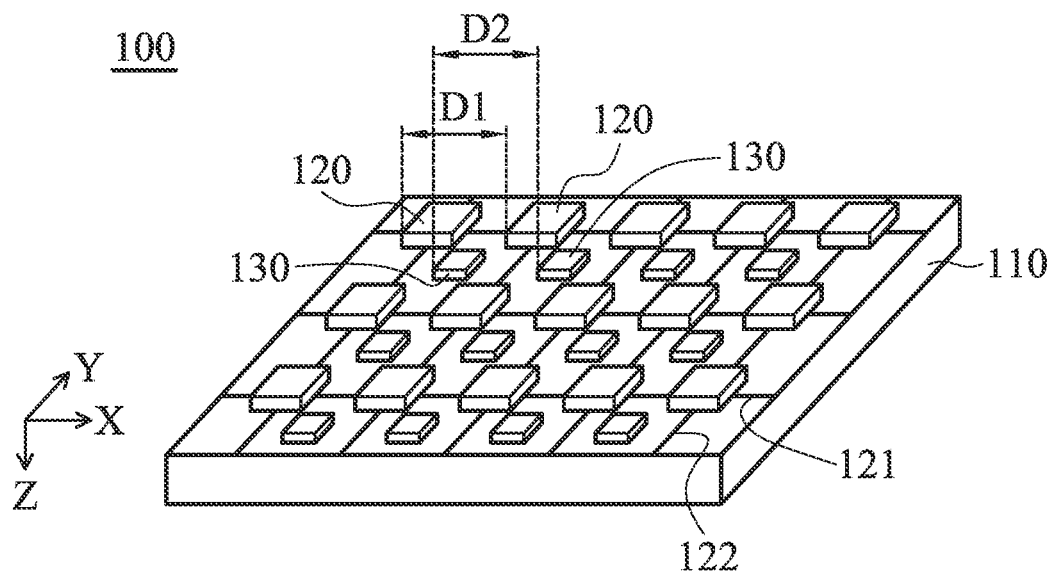
FIG. 2 is a perspective view of an electronic device according to another embodiment of the disclosure.

FIG. 1 is a schematic view of a part of an electronic device according to an embodiment of the disclosure. FIG. 2 is a perspective view of an electronic device according to another embodiment of the disclosure. Please refer to FIG. 1 and FIG. 2. The electronic device 100 may at least include a substrate 110 and a plurality of treatment components 120.

In some embodiments, the substrate 110 may be a glass, a flexible substrate, etc., but the disclosure is not limited thereto. The treatment components 120 may be disposed on the substrate 110. Furthermore, the treatment components 120 may include a first treatment component and a second treatment component, and the first treatment component and the second treatment component are independently controlled. For example, the first treatment component and the second treatment component may be controlled by different active components (such as thin film transistors (TFTs)) or different signals provided by a control circuit 140. That is, in some embodiments, the first treatment component and the second treatment component may provide signals with different parameters at the same time, but the disclosure is not limited thereto. In some embodiments, the first treatment component and the second treatment component may also provide signals with the same parameters at the same time. In other embodiments, when the first treatment component provides the signal, the second treatment component may not provide the signal, but the disclosure is not limited thereto. In addition, the treatment components 120 may be disposed on the substrate 110 in an array.

In some embodiments, each of the treatment components 120 may include a light-emitting component for providing a light signal. In addition, the light-emitting component may be the OLED, the mini LED, the micro LED, the quantum dot LED, or a combination thereof, but the disclosure is not limited thereto. In some embodiments, each of the treatment components 120 may include a heating component for providing a heat signal. In addition, the heating component may be a far infrared ray generator, but the disclosure is not limited thereto. In some embodiments, each of the treatment components 120 may include an ultrasound component for providing an ultrasound signal. In addition, the ultrasound component may be an ultrasound therapy device, but the disclosure is not limited thereto. In some embodiments, each of the treatment components 120 may include an electrotherapy component for providing an electrical stimulation signal. In addition, the electrotherapy component may be an electrical stimulation therapy device, but the disclosure is not limited thereto. Furthermore, each of the treatment components 120 may include at least one of the above components or a combination thereof.

In the embodiments, the electronic device 100 may further include a plurality of signal lines 121, a plurality of signal lines 122, a plurality of sensing components 130 and the control circuit 140.

The signal lines 121 and the signal lines 122 may be electrically connected to the treatment components 120. In the embodiment, the signal lines 121 and the signal lines 122 may respectively data lines or gate lines, but the disclosure is not limited thereto.

The sensing components 130 may be disposed on the substrate 110, and the sensing components 130 may be disposed adjacent to the treatment components 120. In addition, the sensing components 130 may also be electrically connected to the corresponding signal lines thereof (not shown). Furthermore, the sensing components 130 may also be disposed on the substrate 110 in the array. In the embodiment, a pitch D1 between two of the treatment components 120 adjacent to each other may be substantially the same as a pitch D2 between two of the sensing components 130 adjacent to each other, but the disclosure is not limited thereto. In some embodiments, the pitch D1 (or the pitch D2) is measured, for example, by a distance from a center of one of two of the treatment components 120 (or the sensing components 130) adjacent to each other to a center of another one of two of the treatment components 120 (or the sensing components 130) adjacent to each other. In some embodiments, the pitch D1 (or the pitch D2) is measured, for example, by a distance from a rightmost side of one of two of treatment components 120 (or the sensing components 130) adjacent to each other to a rightmost side of another one of two of the treatment components 120 (or the sensing components 130) adjacent to each other. In some embodiments, the pitch D1 (or the pitch D2) is measured, for example, by a distance from a leftmost side of one of two of treatment components 120 (or the sensing components 130) adjacent to each other to a leftmost side of another one of two of the treatment components 120 (or the sensing components 130) adjacent to each other.

The control circuit 140 may be disposed in the substrate 110. The control circuit 140 may be electrically connected to the treatment components 120 and the sensing components 130, such that the control circuit 140 may adjust parameters corresponding to the treatment components according to the sensing signal generated by the sensing components 130, so as to control the treatment components 120 to generate the signals with the corresponding parameters. In the embodiments, the control circuit 140 may include a processor, a micro controller unit (MCU) or an integrated circuit, but the disclosure is not limited thereto.

In some embodiments, each of the sensing components 130 may include a biosensor 131 and an image sensor 132, as shown in FIG. 1. In addition, the biosensor 131 is used to detect a physical quantity of an object 150 to generate a physical quantity signal, and the above physical quantity may include a reflective light, a pH value, a humidity, a temperature, an inflammatory factor, a toxin and an enzyme secreted by a bacteria, an odor, etc., but the disclosure is not limited thereto.

The image sensor 132 is used to sense an image of the object 150 to generate an image sensing signal, and the image sensor 132 may be a charge coupled device (CCD), but the disclosure is not limited thereto. That is, the control circuit 140 may determine a target area of the object 150 according to the image sensing signal generated by the image sensor 132, and determine a state of the target area according to the physical quantity signal generated by the biosensor 131. In the embodiment, the above object 150 is, for example, a human body, and the above target area is, for example, an affected part, but the disclosure is not limited thereto. In some embodiments, the control circuit 140 may, for example, determine the target area and a non-target area according to a signal magnitude of the image sensing signal. In some embodiments, the control circuit 140 may, for example, analyze pixels of the image sensing signal to determine the target area and the non-target area. In addition, the control circuit 140 may determine a state of a sub-area of the target area according to the physical quantity signal generated by the biosensor 131. In some embodiments, the physical quantity is taken as temperature as an example. When the physical quantity signal received by the control circuit 140 is high (for example, the temperature is greater than a first predetermined temperature), the control circuit 140 may determine that the state of the sub-area of the target area is a first state. When the physical quantity signal received by the control circuit 140 is higher (for example, the temperature is greater than a second predetermined temperature), the control circuit 140 may determine that the state of the sub-area of the target area is a second state. The above second predetermined temperature is greater than the above first predetermined temperature, and the first state is different from the second state.

In some embodiments, each of the sensing components 130 may include the biosensor 131 and does not include the image sensor 132. That is, the control circuit 140 may determine the size of the target area of the object 150 and the state of the target area according to the physical quantity signal generated by the biosensor 131. In some embodiments, the physical quantity is taken as temperature as an example. When the physical quantity signal received by the control circuit 140 is low (for example, the temperature is less than or equal to the first predetermined temperature), the control circuit 140 may determine that the location of the biosensor 131 belongs to the non-target area. When the physical quantity signal received by the control circuit 140 is high (for example, the temperature is greater than the first predetermined temperature), the control circuit 140 may determine that the location of the biosensor 131 belongs to the target area (such as the affected part), and the control circuit 140 may determine that the state of the sub-area of the target area is the first state. When the physical quantity signal received by the control circuit 140 is higher (for example, the temperature is greater than the second predetermined temperature), the control circuit 140 may determine that the state of the sub-area of the target area is a second state. The above second predetermined temperature is greater than the above first predetermined temperature, and the first state is different from the second state.

Figure 3:
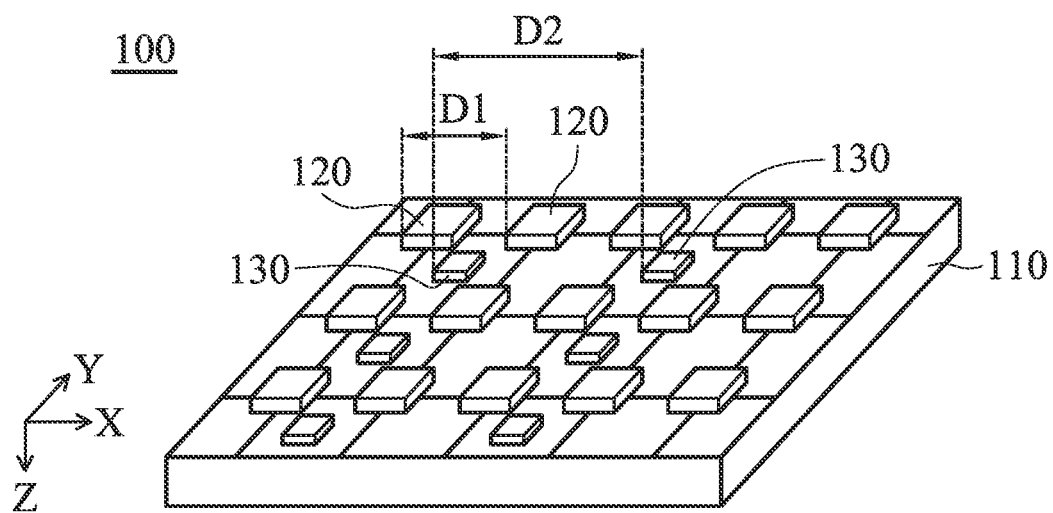
FIG. 3 is a perspective view of an electronic device according to another embodiment of the disclosure.

FIG. 3 is a perspective view of an electronic device according to another embodiment of the disclosure. The electronic device 100 in FIG. 3 is substantially similar to the electronic device 100 in FIG. 1 and FIG. 2. The same or similar elements or components may refer to the description of the embodiment of FIG. 1 and FIG. 2, and the description thereof is not repeated herein. In FIG. 3, a pitch between two of the treatment components 120 adjacent to each other may be different from a pitch D2 between two of the sensing components 130 adjacent to each other. For example, the pitch D1 may be less than the pitch D2, but the disclosure is not limited thereto. Furthermore, the density of the sensing components 130 may be less than the density of the treatment components 120. For example, in an area of the array shown in FIG. 3, the number of the sensing components 130 is less than the number of the treatment components 120. That is, the electronic device 100 may use a small number of sensing components 130 and a larger number of treatment components 120.

Figure 4:
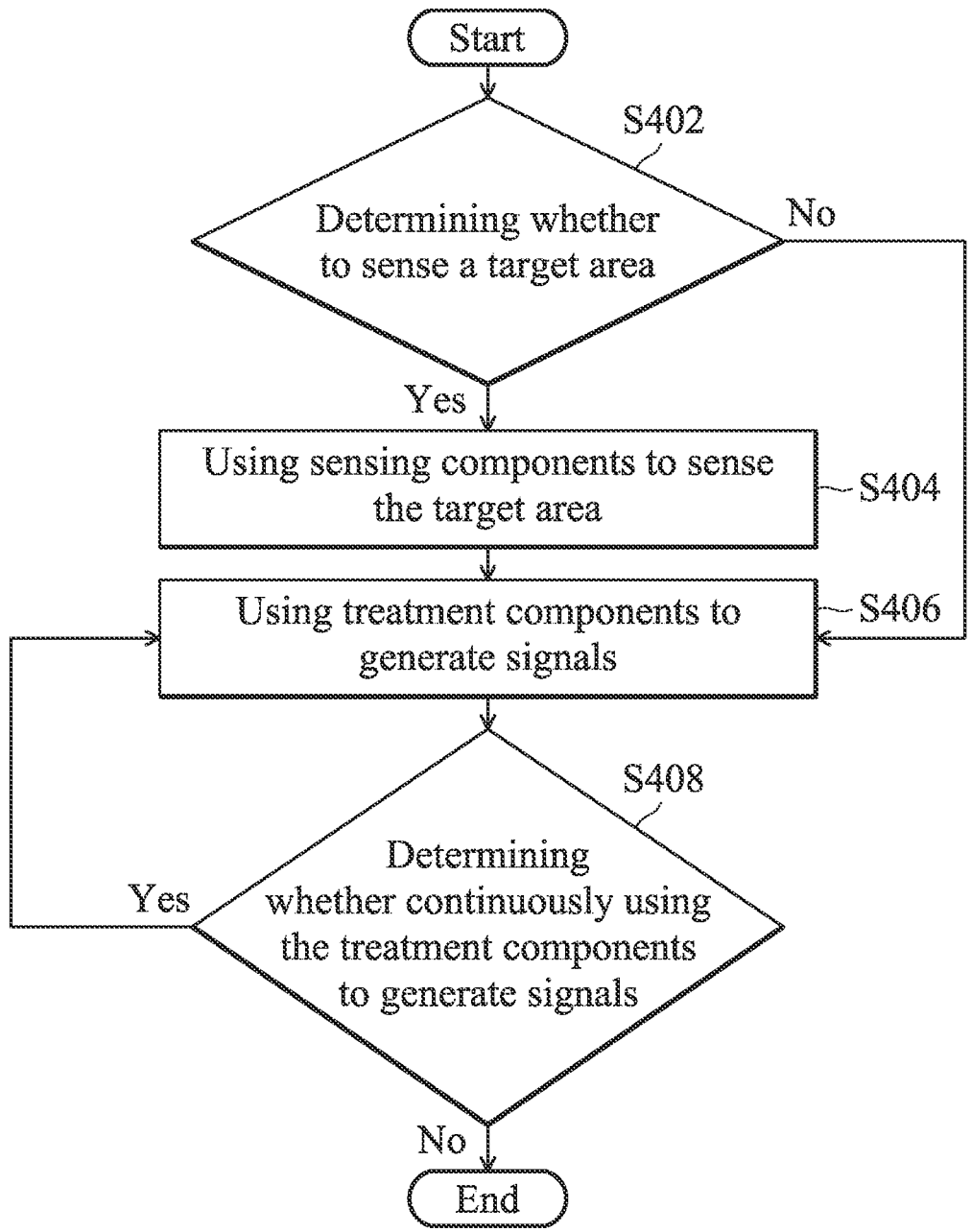
FIG. 4 is a flowchart of an operation method of an electronic device according to an embodiment of the disclosure.

FIG. 4 is a flowchart of an operation method of an electronic device according to an embodiment of the disclosure. In step S402, the method involves determining whether to sense a target area. That is, the control circuit 140 may determine whether to control the sensing components 130 to sense the target area. When determining that the target area is sensed, the method enters step S404. In step S404, the method involves using sensing components to sense the target area. That is, the control circuit 140 may control the treatment components 120 to generate the first lights to irradiate a surface of the object 150, and control the image sensors 132 of the sensing components 130 to sense second lights reflected by the first lights irradiating to the surface of the object 150, such that the sensing image sensors 132 of the sensing components 130 senses the second lights to generate sensing signals to the control circuit 140. Then, the control circuit 140 may calculate the target area according to the sensing signals generated by the image sensors 132. In the embodiment, the object 150 is, for example, the human body, and the target area is, for example, the affected part.

In step S406, the method involves using treatment components to generate signals. That is, after the control circuit 140 calculates the target area, the control circuit 140 may control the treatment components 120 corresponding to the target area to provide the corresponding signals, such as the light signals, but the disclosure is not limited thereto. Therefore, the treatment components 120 may generate the corresponding signals to the target area (such as the affected part), such that the target area (such as the affected part) may receive the energy of the corresponding signals, for example, providing corresponding treatment to the target area (such as the affected part).

On the other hand, following step S402, when determining the target area is not to be sensed, the method directly enters to step S406. In step S406, the method involves using the treatment components to generate the signals. That is, the control circuit 140 may control the treatment components 120 to provide the signals corresponding to the predetermined parameters (such as the light signals with the predetermined parameters) according to the predetermined parameters, but the disclosure is not limited thereto. Therefore, the treatment components may generate signals to the target area (such as the affected part), such that the target area (such as the affected part) may receive the energy of the corresponding signals, for example, providing corresponding treatment to the target area (such as the affected part).

In step S408, the method involves determining whether continuously using the treatment components to generate signals. When determining continuously using the treatment components to generate signals, the method returns to step S406, the control circuit 140 may continuously control the treatment components to generate the signals to the target area. When determining not continuously using the treatment components to generate signals, the operation process of the electronic device 100 is finished.

Figure 5:
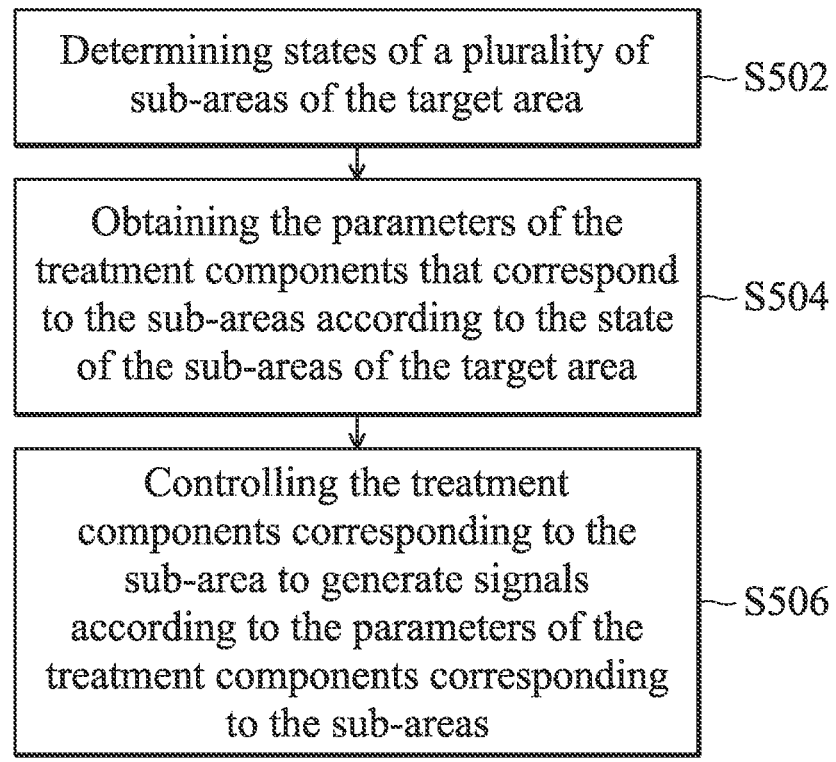
FIG. 5 is detailed flowchart of step S406 in FIG. 4.

FIG. 5 is detailed flowchart of step S406 in FIG. 4. In step S502, the method involves determining states of a plurality of sub-areas of the target area. That is, the control circuit 140 may control the biosensors 131 of the sensing components 130 to sense the physical quantity of the sub-areas of the target area to generate physical quantity signals that correspond to the above sub-areas. Then, the control circuit 140 may calculate the states of the sub-areas of the target area (such as the affected part) according to the physical quantity signals corresponding to the above sub-areas.

Figure 6:
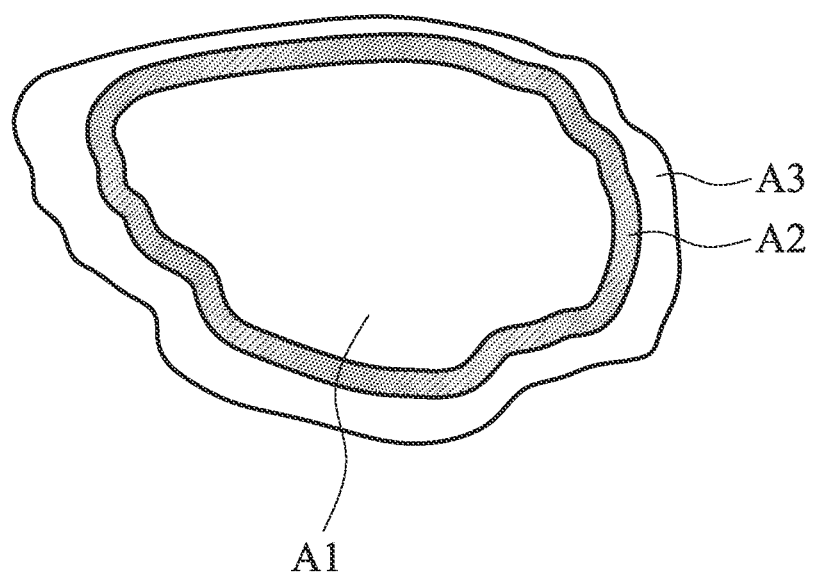
FIG. 6 is a schematic view of sub-areas of a target area according to an embodiment of the disclosure.

In the embodiment, the sub-areas of the target area include, for example, sub-area A1, sub-area A2 and sub-area A3, as shown in FIG. 6. In addition, sub-area A1, sub-area A2 and sub-area A3 are in different states. In some embodiments, for example, sub-area A1 may correspond to an inflammation state, sub-area A2 may correspond to a granulation/cell proliferation state, and sub-area A3 may correspond to a remodeling state, but the disclosure is not limited thereto.

In step S504, the method involves obtaining the parameters of the treatment components that correspond to the sub-areas according to the state of the sub-areas of the target area. That is, after the control circuit 140 calculates the state of the sub-area A1, of sub-area A2 and of sub-area A3, the control circuit 140 may refer to a lookup table to obtain the first parameter of the treatment components 120 corresponding to sub-area A1, the second parameter of the treatment components 120 corresponding to sub-area A2 and the third parameter of the treatment components 120 corresponding to sub-area A3.

In the embodiment, each of the treatment components 120 is taken as a light-emitting component as an example. The first parameter may include a first signal wavelength and a first signal strength. The second parameter may include a second signal wavelength and a second signal strength. The third parameter may include a third signal wavelength and a third signal strength. In some embodiments, for example, the first signal wavelength may be 405 nanometers (nm) to 470 nanometers, the second signal wavelength may be 660 nanometers to 810 nanometers, the third signal wavelength may be 590 nanometers to 800 nanometers, and the first signal strength, the second signal strength and the third signal strength may be 0.1 mW/cm$^2$ to 150 mW/cm$^2$, but the disclosure is not limited thereto. In some embodiments, the first signal strength, the second signal strength, and the third signal strength may be the same. In some embodiments, the first signal strength, the second signal strength, and the third signal strength may be different. In some embodiments, the signal strength may be proportional to the signal wavelength. For example, when the signal wavelength increases, the signal strength may increase. Otherwise, when the signal wavelength decreases, the signal strength may decrease.

In step S506, the method involves controlling the treatment components corresponding to the sub-area to generate signals according to the parameters of the treatment components corresponding to the sub-areas. That is, the control circuit 140 may control the treatment components 120 corresponding to the sub-area A1 to generate the first signals with the first parameter according to the first parameter of the treatment components 120 corresponding to the sub-area A1. The control circuit 140 may control the treatment components 120 corresponding to the sub-area A2 to generate the second signals with the second parameter according to the second parameter of the treatment components 120 corresponding to the sub-area A2. The control circuit 140 may control the treatment components 120 corresponding to the sub-area A3 to generate the third signals with the third parameter according to the third parameter of the treatment components 120 corresponding to the sub-area A3. Therefore, the treatment components 120 may respectively provide the first signals, the second signals and the third signals to the sub-area A1, the sub-area A2 and the sub-area A3 of the target area (such as the affected part), such that the sub-area A1, the sub-area A2 and the sub-area A3 may receive the energies of the signals with different parameters, for example, providing different treatments for the sub-area A1, the sub-area A2 and the sub-area A3.

Figure 7:
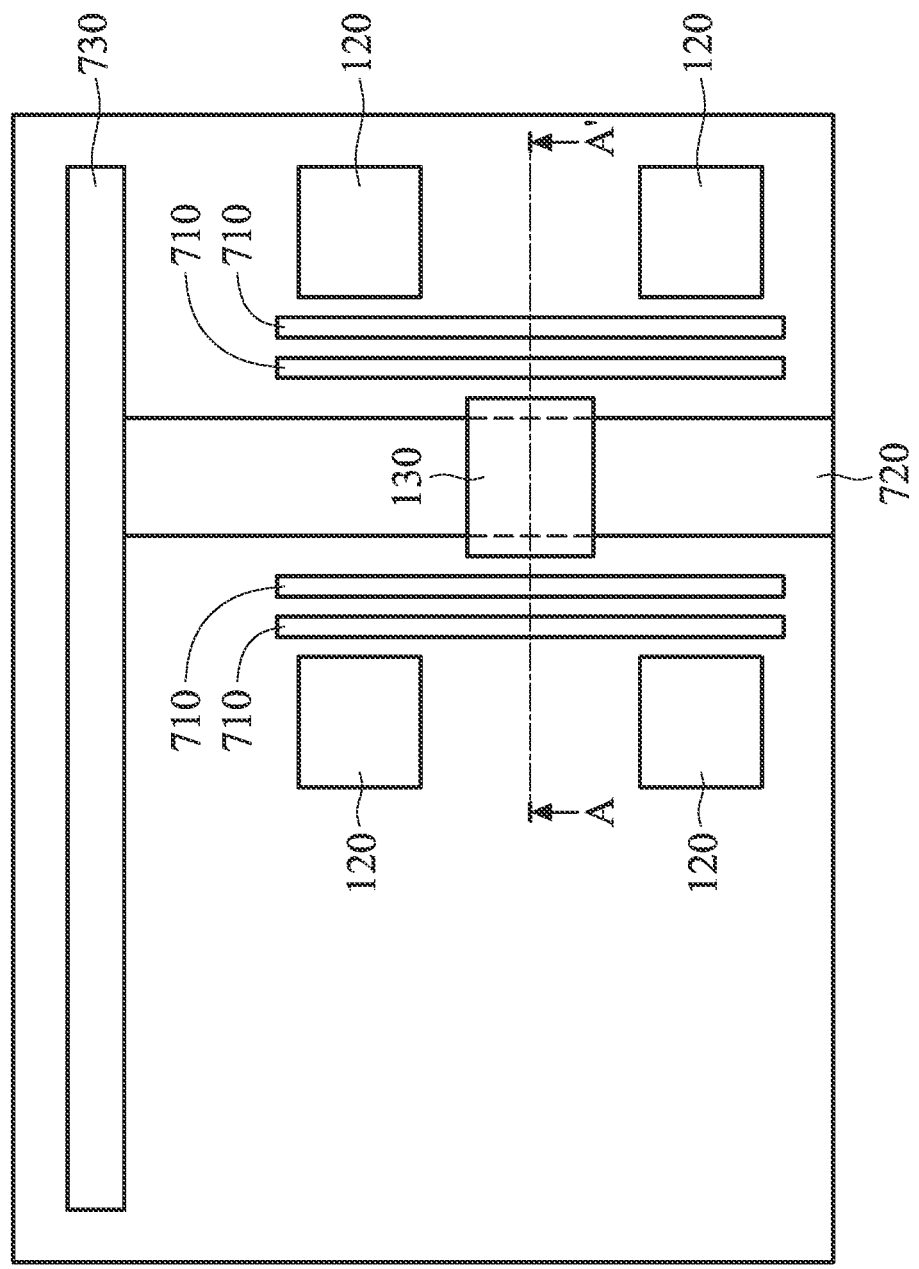
FIG. 7 is a top view of a part of an electronic device according to an embodiment of the disclosure.
Figure 8:
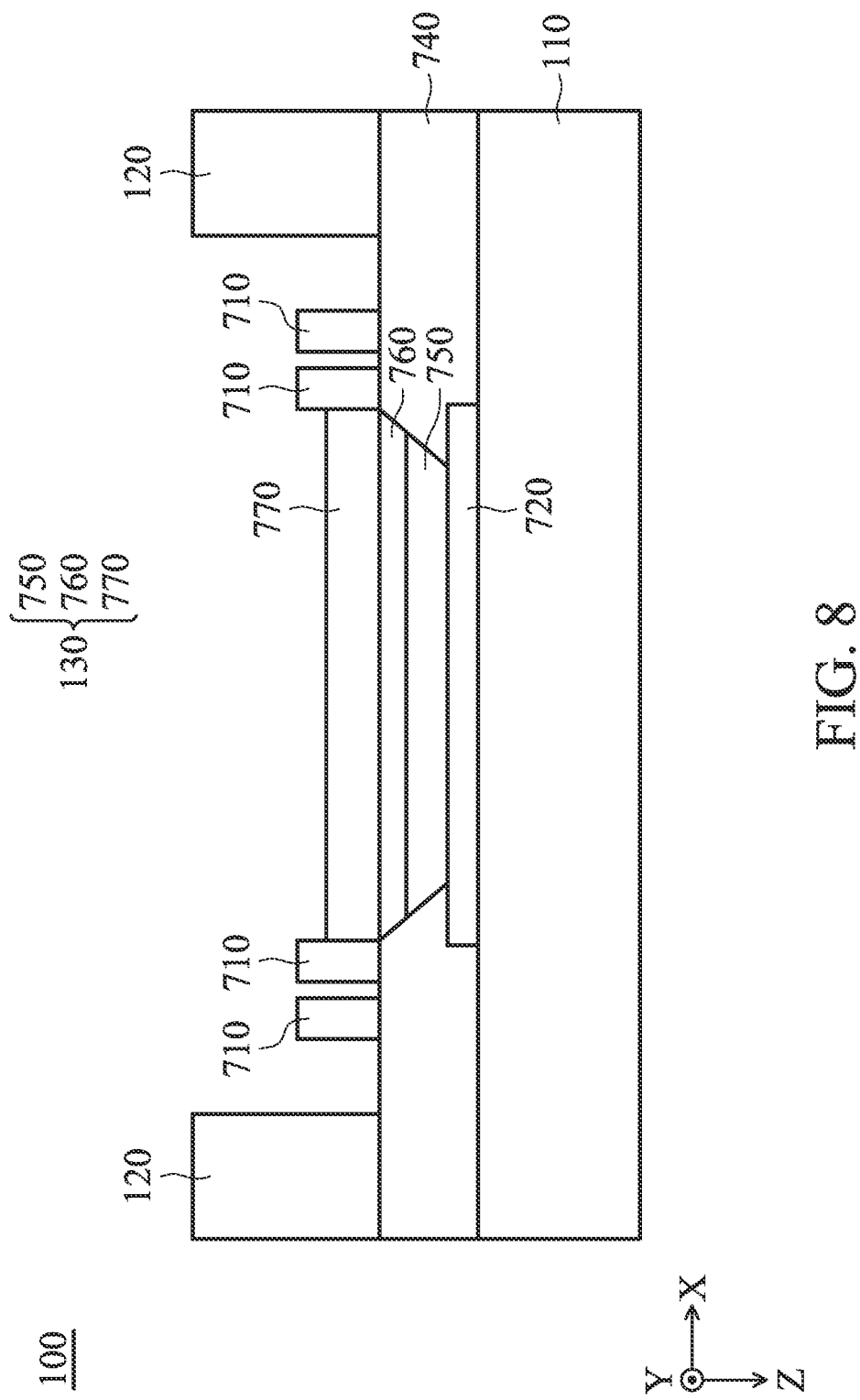
FIG. 8 is a cross-sectional view of A-A' in FIG. 7.

FIG. 7 is a top view of a part of an electronic device according to an embodiment of the disclosure. FIG. 8 is a cross-sectional view of A-A' in FIG. 7. Please to refer to FIG. 7 and FIG. 8. The electronic device 100 may include a substrate 110, treatment components 120, the sensing components 130, retaining walls 710, a metal layer 720, an electrode and a photoresist ink layer 740.

The metal layer 720 is disposed on the substrate 110. In some embodiments, the material of the metal layer 720 may be copper (Cu), but the disclosure is not limited thereto. The sensing components 130 are disposed on the metal layer 720. The sensing components 130 may be electrically connected to the electrode 730 through the metal layer 720, such that the sensing components 130 may be electrically connected to a control circuit (such as the control circuit 140 of FIG. 1) through the electrode 730, and then the sensing components 130 may transmit the sensing signal to the control circuit 140 or the control circuit may provide the control signals to control the sensing components 130. In addition, each of the sensing components 130 may electrically connected to an active component (such as a thin film transistor), so as to be controlled through the active component. In some embodiments, the sensing components 130 in a Y direction 130 may be electrically connected to the electrode 730 through the same metal layer 720, but the disclosure is not limited thereto. In some embodiments, the sensing components 130 in the Y direction may be electrically connected to the electrode 730 through the different metal layer 720, but the disclosure is not limited thereto.

Furthermore, each of the sensing components 130 includes a bottom electrode 750, a semiconductor layer 760 and a top electrode 770. The bottom electrode 750 is disposed on the metal layer 720. The semiconductor layer 760 is disposed on the bottom electrode 750. The top electrode 770 is disposed on the semiconductor layer 760. In some embodiments, the bottom electrode 750 and the metal layer 720 may be directly contacted, the semiconductor layer 760 and the bottom electrode 750 may be directly contacted, and the top electrode 770 and the semiconductor layer 760 may be directly contacted, but the disclosure is not limited thereto. In some embodiments, the bottom electrode 750 may be a multilayer structure, and the material of the bottom electrode 750 may be gold (Au) or nickel (Ni), but the disclosure is not limited thereto. In some embodiments, an intermediate layer may also be included between the bottom electrode 750 and the metal layer 720, so as to increase a boding effect between the bottom electrode 750 and the metal layer 720.

In addition, the photoresist ink layer 740 is disposed on the substrate 110. The treatment components 120 are disposed on the photoresist ink layer 740. The retaining walls 710 are disposed on the photoresist ink layer 740 and located between the treatment components 120 and the sensing components 130 in an X direction. In some embodiments, a height of the retaining walls is, for example, 0.5 micrometers (um) to 10 micrometers, a width of the retaining walls is, for example, 5 micrometers to 100 micrometers. In addition, in FIG. 7 or FIG. 8, the number of the retaining walls 710 between the treatment components 120 and the sensing components 130 is shown as two, but the disclosure is not limited thereto. In some embodiment, the number of retaining walls 710 may be 1, 3, 4, or 5. Therefore, the situation of the overflow of wet process materials may be improved.

The treatment components 120 may also be electrically connected to an electrode (not shown) through a metal layer (not shown), such that the treatment components 120 may be electrically connected to a control circuit (such as the control circuit of FIG. 1) through the electrode, and then the control circuit may provide the control signals to control the treatment components 120. In addition, each of the treatment components 120 may be electrically connected to an active component (such as a thin film transistor), so as to be controlled by the active component. In some embodiments, the treatment components 120 in the Y direction may be electrically connected to the electrode through the same metal layer, but the disclosure is not limited thereto. In some embodiments, the treatment components 120 in the Y direction may be electrically connected to the electrode through the different metal layer, but the disclosure is not limited thereto.

In summary, according to the electronic device and the operation method thereof disclosed by the embodiments of the disclosure, the treatment components are disposed on the substrate, wherein the treatment component includes the first treatment component and the second treatment component, and the first treatment component and the second treatment component are independently controlled and provide the signals with the different parameters at the same time. In addition, the sensing components and the control circuit are disposed on the substrate, the sensing components and the treatment components are disposed adjacent to each other in the array. The control circuit adjusts the parameters of the treatment components according to the sensing signals generated by the sensing components, so as to control the treatment components to generate the signals with the corresponding parameters. Therefore, the convenience of use may be increased, or the treatment effect on the target area may be increased.

While the disclosure has been described by way of examples and in terms of the preferred embodiments, it should be understood that the disclosure is not limited to the disclosed embodiments. On the contrary, it is intended to cover various modifications, combinations, and similar arrangements (as would be apparent to those skilled in the art). Therefore, the scope of the appended claims should be accorded the broadest interpretation to encompass all such modifications, combinations, and similar arrangements.

What is claimed is:

1. An electronic device, comprising:
    a plurality of treatment components, comprising a first treatment component and a second treatment component, wherein each of the first treatment component and the second treatment component comprises a light-emitting component;
    a first sensing component, disposed between the first treatment component and the second treatment component;
    a retaining wall, disposed between the first treatment component and the first sensing component;
    a photoresist ink layer, wherein the first treatment component, the second treatment component, the retaining wall and a part of the first sensing component are disposed on the photoresist ink layer, and another part of the first sensing component is disposed within the photoresist ink layer; and
    a control circuit, electrically connected to the first treatment component, the second treatment component and the first sensing component;
    wherein the first treatment component and the second treatment component are independently controlled by the control circuit.

2. The electronic device according to claim 1, wherein the plurality of treatment components are disposed in an array.

3. The electronic device according to claim 1, further comprising a second sensing component, wherein the first sensing component and the second sensing component are disposed adjacent to the first treatment component and the second treatment component.

4. The electronic device according to claim 3, wherein a pitch between the first treatment component and the second treatment component adjacent to each other is the same as a pitch between the first sensing component and the second sensing component adjacent to each other.

5. The electronic device according to claim 3, wherein a pitch between the first treatment component and the second treatment component adjacent to each other is different from a pitch between the first sensing component and the second sensing component adjacent to each other.

6. The electronic device according to claim 3, wherein each of the first sensing component and the second sensing component comprises a biosensor and an image sensor.

7. The electronic device according to claim 1, further comprising a substrate, wherein the plurality of treatment components are disposed on the substrate.

8. The electronic device according to claim 7, wherein the first treatment component and the second treatment component provide signals with different parameters at the same time.

9. The electronic device according to claim 8, wherein the substrate comprises a first sub-area and a second sub-area, the first treatment component provides a first signal with a first parameter in the first sub-area, and the second treatment component provides a second signal with a second parameter in the second sub-area.

10. An operation method of an electronic device, comprising:
    providing a substrate;
    providing a plurality of treatment components on the substrate, wherein the plurality of treatment components comprise a first treatment component and a second treatment component, and each of the first treatment component and the second treatment component comprises a light-emitting component;
    providing a first sensing component on the substrate, wherein the first sensing component is disposed between the first treatment component and the second treatment component;
    providing a retaining wall on the substrate, wherein the retaining wall is disposed between the first treatment component and the first sensing component;
    providing a photoresist ink layer on the substrate, wherein the first treatment component, the second treatment component, the retaining wall and a part of the first sensing component are disposed on the photoresist ink layer, and another part of the first sensing component is disposed within the photoresist ink layer; and using the first treatment component and the second treatment component to provide signals with different parameters at the same time.

11. The operation method of the electronic device according to claim 10, wherein the substrate comprises a first sub-area and a second sub-area, the first treatment component provides a first signal with a first parameter in the first sub-area, and the second treatment component provides a second signal with a second parameter in the second sub-area.

12. The operation method of the electronic device according to claim 10, wherein the plurality of treatment components are disposed in an array.

13. The operation method of the electronic device according to claim 10, further comprising:
providing a second sensing component on the substrate, wherein the first sensing component and the second sensing component are disposed adjacent to the first treatment component and the second treatment component.

14. The operation method of the electronic device according to claim 13, wherein a pitch between the first treatment component and the second treatment component adjacent to each other is the same as a pitch between the first sensing component and the second sensing component adjacent to each other.

15. The operation method of the electronic device according to claim 13, wherein a pitch between the first treatment component and the second treatment component adjacent to each other is different from a pitch between the first sensing component and the second sensing component adjacent to each other.

16. The operation method of the electronic device according to claim 13, wherein each of the first sensing component and the second sensing component comprises a biosensor and an image sensor.

17. The operation method of the electronic device according to claim 13, further comprising:
providing a control circuit on the substrate, wherein the control circuit is electrically connected to the first treatment component, the second treatment component, the first sensing component and the second sensing component.

* * * * *